United States Patent [19]
Bucalo

[11] 3,961,631
[45] June 8, 1976

[54] METHODS FOR APPLYING SURGICAL SPLINTS

[75] Inventor: Louis Bucalo, Holbrook, N.Y.

[73] Assignee: Investors In Ventures, Inc., New York, N.Y.

[22] Filed: June 20, 1974

[21] Appl. No.: 481,136

[52] U.S. Cl. .............................. 128/334 R; 3/1; 128/1 R
[51] Int. Cl.² ............... A61B 17/12; A61F 1/24
[58] Field of Search ........... 128/1 R, 334 R, 334 C, 128/348, 350 R, 351, 325, 92.87; 3/1, 1.4

[56] References Cited
UNITED STATES PATENTS

| | | | |
|---|---|---|---|
| 2,127,903 | 8/1938 | Bowen | 128/335.5 X |
| 3,422,813 | 1/1969 | Braley et al. | 128/1 R |
| 3,687,129 | 8/1972 | Nuwayser | 128/1 R |
| 3,786,817 | 1/1974 | Palma | 128/334 R |
| 3,805,776 | 4/1974 | Thiele | 128/92 G |

OTHER PUBLICATIONS

Searle Phamplet – "Hernia – The Injection Treatment" 1935.
The Bulletin – Dow Corning Pub. – vol. 14, No. 1, Jan. 1972.

*Primary Examiner*—Dalton L. Truluck
*Attorney, Agent, or Firm*—Steinberg & Blake

[57] ABSTRACT

A surgical procedure wherein tissue which normally covers a body part is displaced away from a portion thereof to expose the latter portion of the body part so that a given treatment can be performed thereon. This exposed portion of the body part is covered with a layer of a highly viscous semisolid substance. Then the tissue is returned to a position covering the semisolid substance. In this way this semisolid substance becomes situated between the previously exposed portion of the body part and the tissue.

6 Claims, 10 Drawing Figures

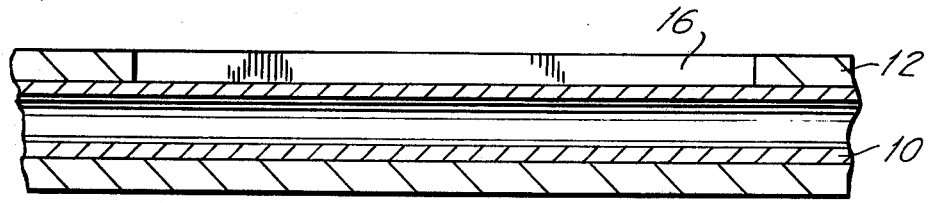
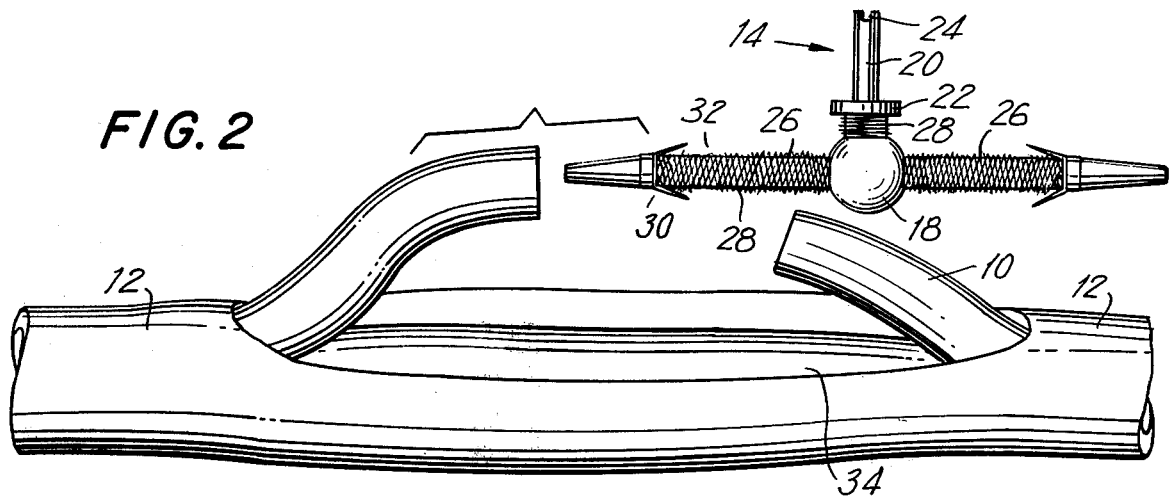
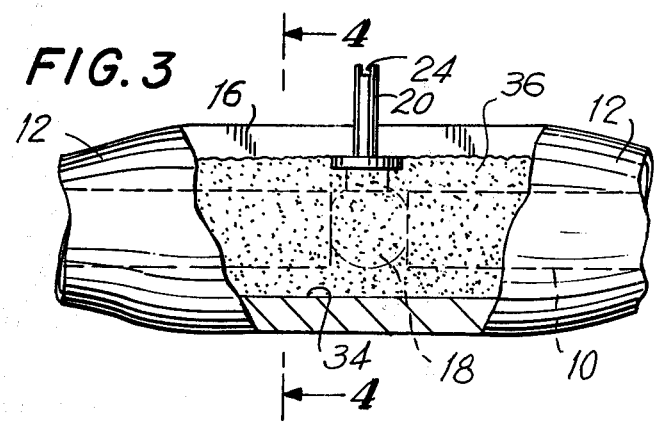
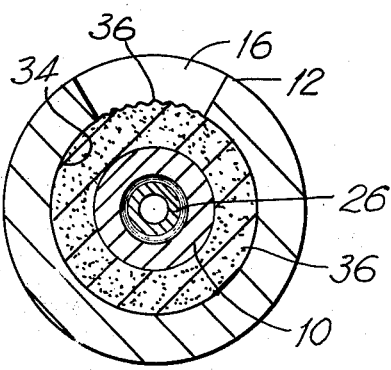
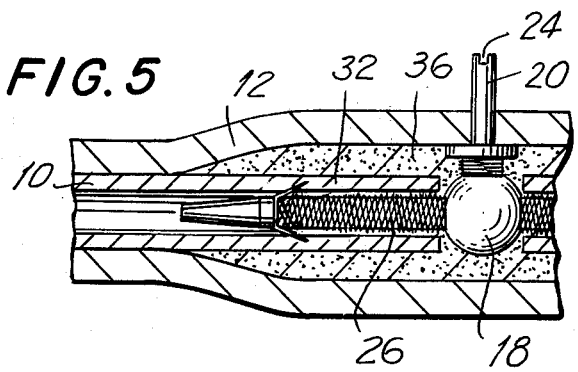

3,961,631

METHODS FOR APPLYING SURGICAL SPLINTS

BACKGROUND OF THE INVENTION

The present invention relates to surgical procedures.

Many surgical procedures require treating a body part which normally is covered by a tissue such as a relatively tough, strong muscular tissue. For example tendons are covered by such a tissue. Also tubular body parts such as vasa deferentia are covered by such tissue.

In order to treat such body parts, the tissue is initially displaced away from a portion of the body part in order to have access to the thus-exposed portion of the body part to enable a treatment to be carried out thereon. After the treatment is completed the tissue is returned, but of course the initial connection between the tissue and the body part has been ruptured. Therefore, the returned tissue only loosely encloses the previously exposed portion of the body part which received the surgical treatment. As a result, the treated portion of the body part is not properly protected by the returned covering tissue, and healing does not take place in the best possible manner. Also, in the case of a vasectomy, reanastomosis or recanalization takes place.

SUMMARY OF THE INVENTION

It is accordingly a primary object of the present invention to provide a method which will avoid disadvantages inherent in conventional surgical procedures as set forth above.

In particular it is an object of the present invention to provide a method for applying to the treated portion of the body part a surgical splint which will protect the treated portion of the body part in a manner enhancing the healing thereof so that healing will take place more rapidly than would otherwise be the case.

Also it is an object of the present invention to provide a method for applying a surgical splint in such a way that the surgical splint exerts a pressure on the treated portion of the body part for promoting healing.

It is furthermore an object of the present invention to provide a surgical splint which can be absorbed into the body, so that it will remain only temporarily in the body, or which will not be absorbed so that it will be permanent.

In addition, it is an object of the present invention to provide a surgical splint which presents particular advantages in connection with an implant which is received in a tubular body part.

Yet another object of the present invention is to provide a surgical splint which is of particular advantage in connection with vas valves.

A still further object of the invention is to provide a surgical splint which is of particular advantage in connection with vasectomies.

According to the invention the surgical procedure includes the steps of displacing tissue which normally covers a body part away from a portion of the body part to expose the latter portion thereof so that a given treatment can be performed on the thus-exposed portion of the body part. The exposed portion of the body part is then covered with a layer of a highly viscous semisolid substance. Then the tissue is returned to a position covering the semisolid substance which thus becomes situated between the previously exposed portion of the body part and the returned tissue.

BRIEF DESCRIPTION OF DRAWINGS

The invention is illustrated by way of example in the accompanying drawings which form part of this application and in which:

FIG. 1 is a fragmentary schematic longitudinal sectional elevation of a tubular body part and tissue surrounding the latter;

FIG. 2 illustrates the body part and tissue of FIG. 1 after it has been acted upon during a surgical procedure in connection with the introduction of an implant which in the illustrated example is a vas valve;

FIG. 3 shows a further stage in the surgical procedure when the vas valve of FIG. 2 has been introduced into the tubular body part which is shown in FIG. 3 covered with a semisolid substance during the return of the surrounding tissue;

FIG. 4 is a schematic transverse section of the arrangement shown in FIG. 3, taken along line 4—4 of FIG. 3 in the direction of the arrows;

FIG. 5 is a fragmentary longitudinal sectional elevation of the final stage of the surgical procedure when the tissue has been returned, this arrangement being illustrated schematically in FIG. 5;

DESCRIPTION OF PREFERRED EMBODIMENTS

Figure 6:
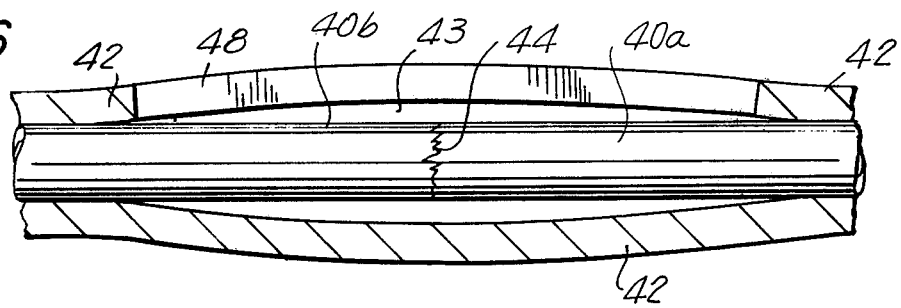
FIG. 6 illustrates surgical procedures for tendons.

Referring to FIG. 1, there is schematically illustrated therein a tubular body part which in the illustrated example is a vas deferens 10. As is well known, this tubular body part 10 is surrounded and covered by a sheath of tissue 12, which is a relatively strong muscular tissue.

In order to introduce an implant into the vas 10, it is necessary to carry out a surgical procedure which involves cutting across the vas 10 after the tissue 12 has been displaced therefrom. For this purpose sheath 12 is slit at 16. During the surgical procedure the vas 10 is pulled out of the surrounding tissue 12 and cut through so as to provide in this way a pair of separated vas portions. During the surgical procedure, the surgeon will maintain the tissue 12 displaced away from portions of the body part 10, in the manner shown schematically in FIG. 2.

Thus, FIG. 2 illustrates schematically exposed portions of the body part 10 with the tissue 12 displaced therefrom. The surgeon will then insert the vas valve 14 at its opposed end regions into the exposed portions of the vas deferens 10. The vas valve 14 has a central housing portion 18 in which a movable valve member is housed. For example, a rotary valve member is connected to the rotary stem 20 which extends upwardly through the neck 22 of the housing 18. The stem 20 is provided at its top end with a slot 24 so that a suitable instrument similar to the tip of a screwdriver can be introduced into the slot 24 for turning the stem 20. The interior of the housing 18 communicates with the interiors of a pair of tubular valve portions 26 which terminate in open ends so that the passage formed by the lumen of the vas 10 will communicate through the tubular portions 26 of the valve 14 with the valve member in the housing 18. The tubular portions 26 as well as the neck 22 are covered with windings of gold wire 28 which in a well known manner form a means for promoting the ingrowth of tissue. However, the tissue-ingrowth means can take other forms, such as, for example, a porous matrix situated at the tubular portions 26 as well as the neck 22 and provided with pores into which the tissue will grow. In addition, the tubular portions 26 carry rings 30 from which barbs 32 extend. These barbs are flexible and have sharp pointed ends so that when the tubular portions 26 are respectively introduced into the adjoining portions of the vas 10, the barbs 32 will on the one hand prevent removal of the vas valve from the vas and will on the other hand immobilize those portions of the vas which extend from the barbs 32 up to the housing 18. It is these portions which engage the tissue-ingrowth means 28. By thus immobilizing the portions of the vas which engage the tissue ingrowth means, the growth of tissue into the ingrowth means is greatly enhanced.

In accordance with the present invention, after the vas portions 10 shown in FIG. 2 have been pulled onto the tubular valve parts 26 and returned with the valve into the pocket 34 formed by sheath 12, the exposed portions of the body part 10 and the valve structure therebetween are covered with a highly viscous semisolid material 36, which is introduced into the sheath pocket. Thus, FIG. 3 shows in dotted lines the exposed parts of the vas 10 situated on and surrounding the tubular parts 26 of the valve 14, with separate parts of the vas 10 terminating directly next to the housing 18. The tissue 12 is still approximately in the condition shown in FIG. 2 while the semisolid material 36 substantially fills, in pocket 34, the space between the tissue 12 and the previously exposed vas parts as well as the central housing part 18 of the valve, as is apparent from FIGS. 3 and 4.

Thereafter, the surgeon will with sutures, for example, close slit 16 of the tissue 12 so that the sheath 12 surrounds the semisolid substance 36 and assumes a condition as illustrated schematically in FIG. 5 for the body parts and valve structure on one side of the valve housing 18. Of course the body parts and valve structure on the other side will be a mirror image of what is shown in FIG. 5.

It will be noted that FIG. 4 clearly illustrates how the tubular valve part 26 is surrounded by a portion of the vas 10 which in turn is surrounded by the semisolid substance 36, with the tissue 12 ready to be closed over the substance 36.

A number of advantages are achieved by the method of the present invention which involves applying the layer 36 of semisolid substance around a portion of the body part 10 before the sheath 12 is closed so that the parts will have the condition shown in FIG. 5. If the layer 36 were not present, then the tissue part 12 would loosely surround the previously exposed portion of the body part 10 since the initial connection therebetween has been ruptured in connection with the displacement of the tissue 12 to expose a portion of the body part 10. As a result the loose portion of the tissue 12 would not exert any inwardly directed radial pressure on the previously exposed portion of the vas 10, and the only pressure available would result from the residual inherent elasticity of the vas 10. In the second place, in this particular application of the present invention which is illustrated in FIGS. 1-5, it is of primary importance to prevent sperm from bypassing the valve. During the time immediately subsequent to the surgical procedures described above and shown in FIGS. 1-5, it is still possible for sperm to travel along the exterior of the tubular parts 26 of the valve 14. Thus, prior to healing there is a possibility that the sperm will bypass the valve. The ingrowth means 28 does not deter to a very large extent any travelling of sperm to an extent sufficient to bypass the valve during the period before tissue has had an opportunity to grow into the ingrowth means 28 to provide a tight seal which effectively prevents sperm from bypassing the valve. Thus, any sperm which become situated between the inner surface of the vas 10 and the tubular part 26 will engage the windings of wire which form the tissue-ingrowth means 28 and will be deflected by these windings around and around the tubular part 26 for achieving an effective prevention of bypassing of the valve. However, it is theoretically possible for at least a minute number of vigorous sperm to travel all the way up to the housing part 18, across the latter, and into the other part of the vas 10 in order to bypass the valve 14 in the period immediately subsequent to the surgical procedures. In order to attempt to avoid such bypassing, the pressure of the vas against the valve is increased, and with the present invention the surgical splint will provide a uniform radial pressure of the vas against the valve. However, with the presence of the mass of semisolid substance 36, it will be necessary for the sperm to travel through this substance, and by reason of the highly viscous nature of the substance 36, it will be impossible for any sperm which escape from one end of the vas 10 to reach the other end thereof on the other side of the housing 18. Thus, the use of the substance 36 is of particular advantage in connection with the implanting of a vas valve.

However, the substance 36 brings about additional important advantages because of its action as a splint. Thus the highly viscous semisolid substance 36 not only fills any free space which otherwise would be present between the returned part of the tissue 12 and the previously exposed portion of the vas 10, but in addition it causes the returned tissue part 12 to act through the mass 36 on the part of the vas 10 which surrounds the tubular part 26 in such a way as to press the vas 10 radially inwardly against the ingrowth means 28. This inwardly directed radical pressure which is achieved by the surgical splint of the invention thus assures an effective pressure of the inner surface of the vas 10 against the tissue ingrowth means 28, and this pressure achieved in this way by the splint 36 of the invention will promote the ingrowth of tissue, resulting in a rapidity of growth of tissue which could not be achieved without the presence of the surgical splint 36. Thus the barbs 32 serve to immobilize the part of the vas 10 which engages the tissue-ingrowth means 28 and the splint 36 serves to press this immobilized part inwardly in a radial direction against the tissue-ingrowth means 28, so that through this combination of features a highly effective ingrowth of tissue in the smallest possible time is assured, and once the ingrowth of tissue takes place a very tight seal is achieved, retaining the vas valve in the desired position and effectively preventing any bypassing of the vas valve by sperm.

Figure 7:
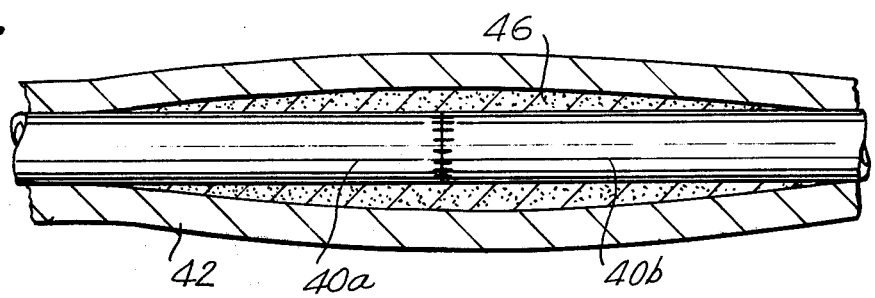
FIG. 7 illustrates the method of the invention for tendons.

It is to be emphasized, however, that the invention is not limited to the specific application shown in FIGS. 1-5. Thus, for example, FIGS. 6 and 7 show, by way of example, how the invention may be utilized in connection with a tendon. In the example of FIG. 6 there is fragmentarily illustrated a tendon 40 which due to injury, for example, has become ruptured and torn so that the tendon parts 40a and 40b must be rejoined. In order to bring about the repair of the injured tendon 40, the surgeon will form a slit 48 and displace the surrounding tissue 42 which is very similar to the tissue 12 described above. This displacement of the tissue 42 will expose the parts 40a and 40b. These exposed tendon parts 40a and 40b are then connected together, as by the sutures 44 schematically shown in FIG. 6.

In accordance with the present invention, before closing pocket 43 formed by sheath 42, a layer 46 of a highly viscous semisolid substance is introduced into the pocket around and covering the joined tendon parts 40a and 40b. Then the tissue 42 is closed around substance 46 with the edges of slit 48 connected together as by suitable sutures. The body parts will now have the condition shown schematically in FIG. 7.

The effect of the presence of the layer 46 in the arrangement shown in FIG. 7 is to greatly stiffen the joined tendon parts 40a and 40b, effectively immobilizing them with respect to each other, so that in effect they form a single elongated relatively stiff body part which will effectively oppose forces which might retard healing. For example if the tendon 40 shown in FIG. 7 is acted upon by a lateral force, this force will act only on the flexible parts of the tendon situated beyond the covering layer 46. The part of the tendon covered by the layer 46 is greatly stiffened by this layer so that it is effectively insulated from the influence of such outside stresses, with the result that the growing together of the interconnected tendon parts 40a and 40b is greatly enhanced and takes place with far greater rapidity and far more reliably than would otherwise be the case.

It is apparent, therefore, that great advantages are achieved by utilizing a surgical splint 36 or 46 in accordance with the present invention, and it is also apparent that the method of the present invention is of general applicability.

The effects which are desired from these surgical splints of the invention are of a temporary nature. Thus, once tissue ingrowth has occurred between the vas 10 and the vas valve in the case of FIGS. 1–5 and once the tendon 40 of FIGS. 6 and 7 has healed, there is no further requirement for the surgical splint. Therefore, in accordance with a further feature of the invention, it is preferred to use for these surgical splints of the invention substances which are capable of being absorbed by the body. In general, it is possible to use for these surgical splints of the invention any highly viscous material which is compatible with the body and which has a consistency similar to that of putty or clay. However it is additionally preferable, in view of the transient requirement of splints as described above, that the substance used for the splint be capable of being absorbed by the body. Thus, among the substances which are preferred are hydrogenated cotton seed oil, hydrogenated vegetable oil, or gelatin. Any of these latter substances on the one hand have the highly viscous semisolid characteristic capable of achieving the effects of the invention and on the other hand are eventually absorbed into the body so that they disappear enabling the exterior tissue to become rejoined with the inner body part which it covers and at the same time achieving for the period required the splint effects of inwardly directed radial pressure which give added rigidity which is of advantage in the case of FIGS. 6 and 7 and which enhance tissue ingrowth in the case of FIGS. 1–5. Of course in connection with a vas valve there is the additional advantage of providing a further barrier to sperm which might otherwise bypass the valve, as set forth above.

Figure 8:
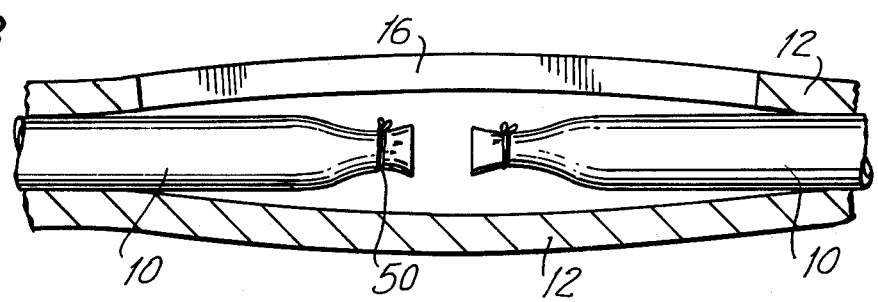
FIG. 8 schematically illustrates a vasectomy.
Figure 9:
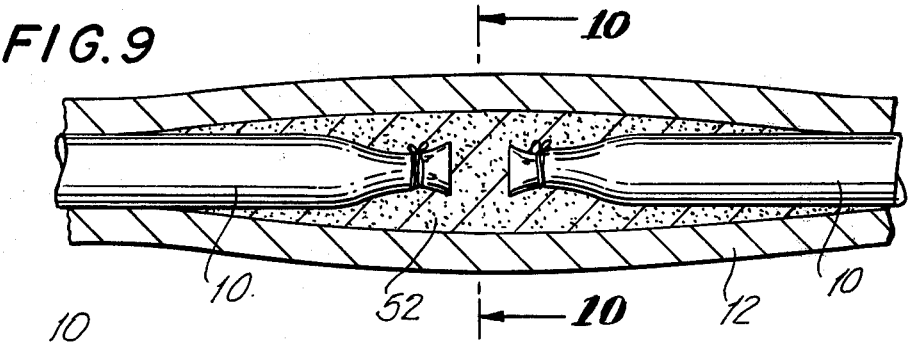
FIG. 9 illustrates a vasectomy of the present invention.
Figure 10:
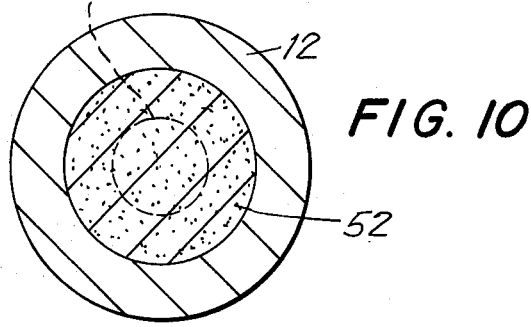
FIG. 10 is a schematic transverse section taken along line 10—10 of FIG. 9 in the direction of the arrows.

FIGS. 8–10 illustrate how the surgical splint of the present invention is of particular advantage in connection with a vasectomy. As may be seen from FIG. 8, which schematically illustrates procedures in connection with a conventional vasectomy, the sheath of tissue 12 is formed with the longitudinal slit 16 so that access may be had to the vas 10, precisely as described above in connection with FIGS. 1–5. During performance of the vasectomy operation, excision of a short length of the vas 10 takes place and the free ends of the vas 10 created in this way are closed off as by tying suture material 50 around the free ends of the vas 10 so as to close the free ends. This is the condition shown in FIG. 8. The conventional vasectomy is completed by closing the slit 16 so that the closed ends of the vas 10 are again surrounded by the tissue 12 with these ends being spaced from each other. While it is true that a vasectomy as described above and shown in FIG. 8 is effective for a large number of individuals, nevertheless there have been documented verified situations where certain individuals having a vasectomy as described above and shown in FIG. 8 nevertheless have not reliably prevented sperm from being included in the ejaculated liquid. In some way, with certain individuals reanastomosis or recanalization occurs. For example it can happen that the ends of the vas shown in FIG. 8 are not tightly closed so that sperm can travel out of one end of the vas along a channel in the interior of the sheath 12 into the other end of the vas. Also, it may happen that the free ends of the vas engage each other and if in this event the free ends are not tightly closed reanastomosis occurs.

In accordance with the present invention, in order to avoid these drawbacks, before the slit 16 is closed a highly viscous semisolid substance 52 is introduced into the pocket of the sheath 12 where the free ends of the vas 10 are located. It will be noted from FIGS. 9 and 10 that this substance 52 not only fills the space between the exterior surface of the vas 10 and the inner surface of the sheath 12, but also this substance 52 fills the space between the ends of the vas 10 where a part of the vas 10 has been excised. Thus, in this case the surgical splint 52 of the present invention will form a barrier of a thick viscous substance through which it is impossible for the sperm to travel. Therefore if it should happen that sperm should escape from one end of the excised vas, this sperm will not be capable of travelling freely into the other end. Instead the sperm will engage the barrier formed by the splint 52 of the present invention.

In this example of FIGS. 8–10 it is desirable to provide for the splint 52 a highly viscous semisolid substance which will not be absorbed into the body. An example of such a substance, which is preferred for the particular application shown in FIGS. 8–10, is silicone oil which while being compatible with the body will not be absorbed into the same so that in this way a permanent barrier will be formed by the splint 52 of the present invention.

What is claimed is:

1. In a surgical procedure, the steps of surgically displacing tissue which normally covers a body part away from a portion of the body part to expose said portion thereof, while leaving said tissue connected with said body part beyond said exposed portion thereof, performing a given surgical treatment on the thus-exposed portion of the body part, thereafter covering the exposed portion of the body part with a highly viscous semisolid substance, and returning the previously displaced tissue to a position covering the semisolid substance and forming with said portion of the body part a pocket in which the semisolid substance becomes situated between the previously exposed portion of the body part and the returned tissue, the body part being tubular while the treatment involves inserting at least part of an implant into the tubular body part so that the semisolid substance presses the tubular body part inwardly radially toward the implant.

2. In a method as recited in claim 1 and wherein the implant carries at its exterior in engagement with the tubular body part a means for promoting ingrowth of tissue, so that the pressure of the tubular body part against the latter means promotes the ingrowth of tissue.

3. In a method as recited in claim 1 and wherein the implant is a vas valve while the tubular body is a vas deferens having at least one end receiving a part of the valve, the semisolid substance covering at least said one vas end to act as a barrier preventing sperm from by-passing the vas valve.

4. In a surgical procedure, the steps of surgically displacing tissue which normally covers a body part away from a portion of the body part to expose said portion thereof, while leaving said tissue connected with said body part beyond said exposed portion thereof, performing a given surgical treatment on the thus-exposed portion of the body part, thereafter covering the exposed portion of the body part with a highly viscous semisolid substance, and returning the previously displaced tissue to a position covering the semisolid substance and forming with said portion of the body part a pocket in which the semisolid substance becomes situated between the previously exposed portion of the body part and the returned tissue, the treatment being a vasectomy with the portion of the body part being formed by severed ends of a vas which is severed and has said ends closed during the vasectomy, said tissue forming when returned a pocket enclosing said substance with the latter situated around and between the closed vas ends to act as a sperm barrier.

5. In a method as recited in claim 4 and wherein said substance is incapable of being absorbed by the body.

6. In a method as recited in claim 5 and wherein the substance is silicone oil.

* * * * *